(12) United States Patent
Josse et al.

(10) Patent No.: US 11,978,202 B2
(45) Date of Patent: May 7, 2024

(54) DEVICE FOR CHARACTERIZING AND COMPARING ERYTHEMAL ZONES

(71) Applicant: PIERRE FABRE DERMO COSMETIQUE, Boulogne Billancourt (FR)

(72) Inventors: Gwendal Josse, Toulouse (FR); Jimmy Le Digabel, Toulouse (FR)

(73) Assignee: PIERRE FABRE DERMO COSMETIQUE, Lavaur (FR)

( * ) Notice: Subject to any disclaimer, the term of this patent is extended or adjusted under 35 U.S.C. 154(b) by 334 days.

(21) Appl. No.: 17/423,889

(22) PCT Filed: Jan. 19, 2020

(86) PCT No.: PCT/EP2020/051207
§ 371 (c)(1),
(2) Date: Jul. 18, 2021

(87) PCT Pub. No.: WO2020/148454
PCT Pub. Date: Jul. 23, 2020

(65) Prior Publication Data
US 2022/0122248 A1    Apr. 21, 2022

(30) Foreign Application Priority Data
Jan. 18, 2019  (FR) ..................................... 19 00477

(51) Int. Cl.
*G06T 7/00* (2017.01)
*A61B 5/00* (2006.01)

(52) U.S. Cl.
CPC .......... *G06T 7/0012* (2013.01); *A61B 5/0077* (2013.01); *G06T 2207/30088* (2013.01)

(58) Field of Classification Search
CPC ......... G06T 7/0012; G06T 2207/30088; A61B 5/0077
(Continued)

(56) References Cited

U.S. PATENT DOCUMENTS 9,763,867 B2 *  9/2017  Perier .................... A61P 43/00
9,814,660 B2 * 11/2017  Perier .................... A61Q 17/04
(Continued)

FOREIGN PATENT DOCUMENTS

DE      198 28 497 A1    12/1999
FR      3005255 A1       11/2014
WO      03/030707 A2      4/2003

OTHER PUBLICATIONS

Anonymous, "Cosmetics—Sun Protection Test Methods—In Vivo Determination of the Sun Protection Factor (SPF)," DIN EN ISO 24444:2010, Mar. 1, 2011. pp. 1-52.

*Primary Examiner* — William D Titcomb
(74) *Attorney, Agent, or Firm* — H&I PARTNERS; C. Andrew Im; Chai Im (57) ABSTRACT

A system to compare erythemal zones includes a multispectral camera to acquire a multispectral image of each compared zone and a computer processing device to retrieve the images acquired by the multispectral camera. The computer processing device includes a memory, a display, an input device and a microprocessor. The system further includes an image processing program configured to perform spectral de-mixing of the acquired images and isolating the erythemal component of the images, and a program to compare the images based on the intensity of the erythemal components of each image.

4 Claims, 3 Drawing Sheets

(58) Field of Classification Search
USPC .......................................................... 382/128
See application file for complete search history.

(56) References Cited

U.S. PATENT DOCUMENTS

| | | | | |
|---|---|---|---|---|
| 2009/0318815 | A1* | 12/2009 | Barnes | A61B 5/444 |
| | | | | 382/128 |
| 2009/0326383 | A1* | 12/2009 | Barnes | A61B 5/417 |
| | | | | 850/1 |
| 2012/0034176 | A1* | 2/2012 | Poigny | C07C 323/20 |
| | | | | 514/552 |
| 2014/0088380 | A1 | 3/2014 | Sprigle et al. | |
| 2015/0287191 | A1* | 10/2015 | Koruga | A61B 5/444 |
| | | | | 382/128 |
| 2015/0313532 | A1* | 11/2015 | Marinkovich | A61B 5/486 |
| | | | | 600/306 |
| 2017/0000406 | A1 | 1/2017 | Schnidar et al. | |
| 2017/0303845 | A1* | 10/2017 | Chen | A61B 5/445 |
| 2018/0066984 | A1* | 3/2018 | Rastegar | G06T 7/0012 |
| 2018/0321139 | A1* | 11/2018 | Helfmann | A61B 5/0082 |
| 2019/0096093 | A1* | 3/2019 | Shinoda | G06T 7/11 |
| 2020/0121243 | A1* | 4/2020 | Anderson | G06T 7/0012 |
| 2020/0176099 | A1* | 6/2020 | Welss | A61B 5/6898 |
| 2020/0200597 | A1* | 6/2020 | Tønnesland | G06T 7/0014 |
| 2022/0202678 | A1* | 6/2022 | Provost | A61K 8/411 |

* cited by examiner

DEVICE FOR CHARACTERIZING AND COMPARING ERYTHEMAL ZONES

RELATED APPLICATIONS

This application is a § 371 application of PCT/EP2020/051207 filed Jan. 19, 2020, which claims priority from French Patent Application No. 19 00477 filed Jan. 18, 2019, each of which is incorporated herein by reference in its entirety

TECHNICAL FIELD

The invention relates to a device for characterizing and comparing erythemal zones of the skin. The invention is more particularly, but not exclusively, adapted to determining a sun protection index, or Sun Protection Factor (SPF), of a photoprotective product intended to be applied on the skin.

BACKGROUND OF THE INVENTION

The development and the evaluation of a cosmetic product requires many tests of which skin irritation tests aiming, for example, to check the safety of a product, or its protection index.

These tests are conducted by exposing the skin, human or animal, to the product or to stress it such as by an exposure to ultraviolet radiation, according to various modalities, then to detect and characterize erythemal zones on the regions thus exposed.

The characterization of erythemal zones is based on a comparison, either between said erythemal zone and healthy skin (without erythema) or between two erythemal zones subjected to different conditions.

The detection of an erythema and its characterization is based on the interpretation of erythemal conditions by a practitioner, for example a dermatologist.

Determining the sun protection factor of a photoprotective product is an example of a test involving the detection and characterization of erythemal zones.

A photoprotective product is a product: cream, lotion, balm or powder containing any component able to absorb, reflect or scatter UV rays, which is intended to be placed in contact with human skin. Such a product acts by reflecting, absorbing or scattering radiation externally to the skin and has no therapeutic action on it.

Alternatively, the photoprotective product is a textile.

The sun protection factor determines the increase of the UV exposure time imparted by the application of the product before this exposure produces an erythema, more commonly designated as "sunburn".

Thus, if a subject exposing itself to a given UV radiation without protection develops an erythema after 5 minutes of exposure to this radiation, the same subject, protected by the application of a photoprotective product having a SPF of 10, will be able to expose itself to this same radiation for 50 minutes before developing erythema.

Determining the sun protection factor (SPF) of such a product involves in vivo tests comprising the exposure of the protected and unprotected skin of a subject to ultraviolet radiation according to controlled modalities.

Thus, determining the sun protection factor of a product applied on the skin is defined by the ISO 24444:2010 standard which consists of an in vivo test performed on the skin of a plurality of subjects.

According to this test, for a given subject, a first portion of the skin, unprotected, that is to say without application of the photoprotective product, is exposed, according to substantially circular spots, to UV radiation according to increasing doses.

A second portion, adjacent to the first portion, is covered by the protective product and exposed, according to substantially circular spots, to UV radiation also according to increasing doses.

An experienced practitioner determines for each of these portions the spot for which the Minimum Erythemal Dose, or MED, is reached, that is to say the spot for which the UV dose received by the skin causes erythema to appear.

Thus, in accordance with the standard, the MED is the lowest dose of ultraviolet (UV) radiation that produces the first perceptible unambiguous erythema, having regular borders and appearing on most of the UV exposure site, within the 16 h to 24 h following the exposure to said UV radiation.

The UV dose corresponding to the MED of the unprotected portion, called MEDu, is lower than the UV dose corresponding to the MED of the protected zone, called MEDp.

Thus, according to this method, the sun protection factor for a given subject, or individual SPF (SPFi) corresponds to the ratio between the MED of the protected zone to the MED of the unprotected zone for this same subject, and SPFi=MEDp/MEDu.

The SPF of the product is the arithmetic mean of all the valid individual SPFi values obtained from all the subjects of the test.

The conditions relating to the source of UV exposure, combining UVA and UVB, to the exposed zones and to the selection of subjects are determined by the ISO 24444:2010 standard.

It should be noted that, according to the standard, the determination of the erythemal zone used for determining the MED is performed "blind" by one or more practitioners who have not participated in the application of the product and in the exposure of the zone considered, consequently not knowing the dose received. This tasks therefore in fact corresponds to a collection of data, subsequently processed anonymously, aiming to characterize a product and not to make a diagnosis.

This test method takes a long time to implement and is based on a series of visual interpretations, inevitably subjective, and dependent on the observation conditions leading to these interpretations. The variety of skin colors, the lighting conditions during the analysis and the visual acuity of the practitioner are as much factors, among others, likely to influence the results.

The reproducibility is all the trickier as the method requires determining the spot having received a UV dose, in practice the smallest dose, corresponding to the appearance of erythema. The exposure doses being discrete and incremental, there may be ambiguity with the spot having received an immediately lower dose and the spot having received an immediately higher dose.

Other skin irritation tests implementing various exposed zones, particularly the safety tests implementing a series of patches, are based on interpretations and comparisons between exposed zones and as a consequence also have an interpretive and subjective part, likely to introduce variability into the results.

Document FR3005255 describes a photogrammetric method wherein an image of the exposed zones is normalized and segmented, with reference to a test pattern. The detection of the erythemal zone is performed via a learning method. This method makes it possible to limit the influence of environmental conditions (e.g., lighting, skin color) but remains linked to an interpretation within the scope of the learning.

Document US2014/0088380 describes a multispectral imaging system used for detecting bruises and pressure ulcers, and uses for this purpose an acquisition according to a reduced number of spectral bands.

Document WO 03/30707 describes a method for determining a minimum erythemal UV dose, by multispectral imaging, using a spectral band of which the intensity of the reflected light can be correlated with the amount of melanin in the skin.

In contrast to the method subject matter of the invention these devices and methods of the prior art do not make use of a spectral de-mixing operation making it possible to extract an erythemal signature in the multispectral image.

OBJECT AND SUMMARY OF THE INVENTION

The object of the invention is a device or system, implementing an automated or semi-automated method, for characterizing and comparing erythemal zones, particularly adapted to determining the sun protection factor (SPF) of a photoprotective product making it possible to limit the influence of the interpretative part, or even to dispense with any interpretation.

Thus, the invention relates to a system for comparing erythemal zones, comprising a multispectral camera for acquiring a multispectral image of the compared zones, a computer processing device comprising memory, display, input and calculation means, capable of retrieving the images acquired by the multispectral camera, comprising an image processing program capable of performing spectral de-mixing of the acquired images and isolating the erythemal component of said images and a program for comparing the images based on the intensity of the erythemal components of each image.

Thus, the system of the invention advantageously uses a multispectral image to extract therefrom the components specific to an erythemal situation and thus facilitate and make reliable the interpretation of the images.

The invention is advantageously implemented according to the embodiments and the variants disclosed below which are to be considered individually or according to any technically effective combination.

Advantageously, the images acquired by the multispectral camera and transmitted to the computer system comprise metadata relating to the conditions for creating erythemal zones and to the conditions for acquiring the images. Thus, the use of these metadata makes it possible to automate all or part of the processing.

According to a particular embodiment, the system subject matter of the invention is adapted to determining the individual sun protection factor (SPFi) of a photoprotective product, the compared images comprising the images of a plurality of sites corresponding to exposures to increasing UV doses and the metadata comprise all or part of the information relating to the product tested, to the corresponding UV doses at the various exposed sites and to the dimension of the exposed zones. Thus, the system subject matter of the invention is compatible with the protocol disclosed in the ISO 24444:2010 standard.

Advantageously, according to this particular embodiment, the comparison program comprises determining for each compared image a response curve giving the intensity of the erythemal component depending on the UV dose. Determining these response curves makes it possible to limit the variability of the results and in some alternative embodiments to eliminate the step of visually determining the MED In one variant of the system of the invention, adapted to determining the SPFi of a photoprotective product, the memory means of the computer device of the system of the invention comprise a threshold or a band of erythemal intensity depending on the UV dose, and the comparison program determines the SPFi by the intersections of this band or of this threshold with the response curves of each compared zone. This variant makes it possible to automatically determine the SPFi.

In another variant, the comparison program determines the SPFi by determining a homothety factor k minimizing the square deviation between the response curves of the compared zones, one of the curves being assigned the factor k. This embodiment makes it possible to determine the SPFi based on all of the sites exposed to the UV doses.

Thus, the invention also relates to a method, for determining the SPFi of a sun protection product from 2 images each comprising a plurality of spots obtained by the exposure of skin to increasing UV doses, one of the series being obtained on skin without protection and the other on skin protected by the product, the two series causing an erythemal character to appear on at least one of the spots, comprising the steps of:

a. acquiring a multispectral image of each of the series;
b. carrying out for each of the images a spectral de-mixing so as to obtain for each spot of each series the intensity of the spectral components corresponding to erythema;
c. determining from the result of step b) a response curve giving the intensity of the erythemal components depending on the UV dose for each of the series; and
d. comparing the response curves thus obtained in order to determine the SPFi.

According to one embodiment of the method of the invention, step d) comprises displaying in false colors the erythemal components of the images of the protected zone and of the unprotected zone, and the pointing on these images, by means of the input means of the computer device zones corresponding to the minimal erythemal doses on each of the images, reporting the erythemal intensity corresponding to the minimal erythemal dose $u_{n1}$ on the response curve of the protected area in order to obtain the corresponding dose $u_{p2}$, reporting the erythemal intensity corresponding to the minimal erythemal dose $u_{p1}$ on the response curve of the unprotected zone in order to obtain the dose $u_{n2}$, determining SPFi by the amount $(u_{p1}+u_{p2})/(u_{n1}+u_{n2})$. This embodiment is fully compliant with the ISO 24444:2010 standard but the determination of the MED is more reliable.

According to another embodiment of the method of the invention, step d) comprises approximating response curves by sigmoids $f_n$, $f_p$ and the SPFi is the k value minimizing the mean square deviation between the functions $f_n$, $f_p$ ranging from the lowest UV dose to the highest UV dose of exposure of the compared zones. This embodiment makes it possible to automatically determine the SPFi by taking into account all of the exposure sites.

Advantageously, step a) comprises acquiring a zone of healthy skin (without erythema) and step b) of spectral de-mixing uses this acquisition for determining the erythemal components.

The system and the method subject matter of the invention further make it possible to automate the characterization of erythemal zones, for this purpose they are advantageously used for carrying out screening in view of selecting the ingredients constituting a product intended for a topical application.

BRIEF DESCRIPTION OF THE DRAWINGS

The invention is disclosed below according to its preferred embodiments, in no way limiting and with reference to FIGS. 1 to 7 wherein:

FIGS. 2A-2B schematically represent the envelope of the spectra obtained from the images from the multi spectral camera, FIG. 2A is comparison between skin without erythema and irritated skin and FIG. 2B is isolated spectrum of the erythemal response;

DETAILED DESCRIPTION OF THE EMBODIMENTS

Figure 1:
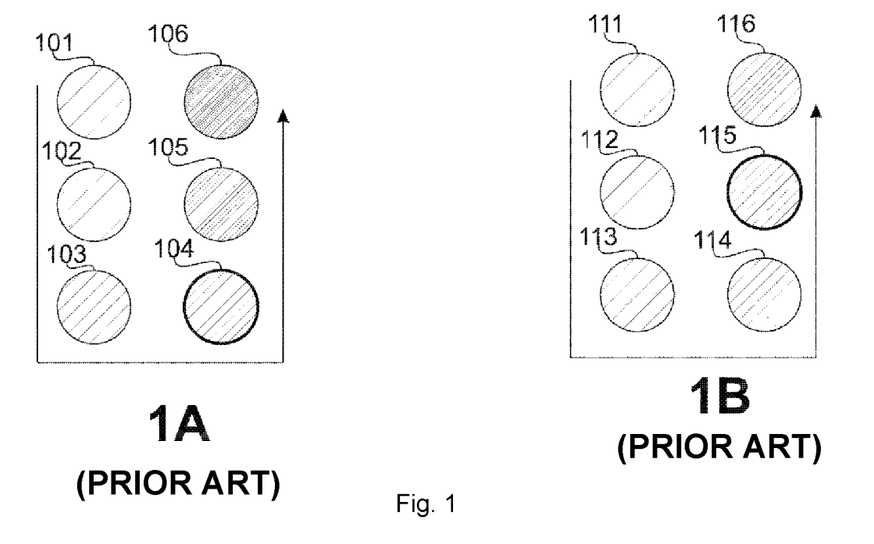
FIGS. 1A-1B relating to the prior art schematically represent two zones comprising a plurality of sites (spots) exposed to increasing UV doses, FIG. 1A an unprotected zone and FIG. 1B a zone protected by a photoprotective product.

FIGS. 1A-1B, relating to the prior art, illustrate the method for determining a SPFi value for a given subject.

In FIG. 1A, zones of the skin of the subject (101 to 106), without protection, the location of which is defined by the standard, are exposed to increasing UV doses. According to one example of embodiment, the UV dose is increasing by a factor 1.25 from one zone to the other, so that the $6^{th}$ exposed zone (106) receives a dose 3 times greater than that of the first exposed zone (101).

The UV dose received by each spot is determined by the exposure time of the spot to the UV source.

In FIG. 1B, the same operation is performed, on the same subject, on zones (111 to 116) this time protected by the product tested.

In order to limit the number of tests, the protection index of the product is presumed, for example in the form of an expected minimum protection index.

Thus, if the presumed minimum protection factor of the product is for example 12, the first zone (111) of the portion protected by the product tested is exposed to a dose 12 times greater than that at which the first zone (101) of the unprotected has been exposed.

The following zones (112 to 116) are exposed to increasing doses, for example according to a factor 1.25 from one zone to another.

The procedure described above and that corresponds to the ISO 24444:2010 standard is a prerequisite to the implementation of the system of the invention that implements a method for analyzing results, in the case of determining the SPF of a product.

FIG. 1A, according to the prior art and with reference to this example, the fourth exposed zone (104) of the unprotected portion is evaluated as being the first, in the increasing order of exposure represented by the broken arrow in this figure, to cause erythema to appear.

Thus, this zone corresponds to a dose 4 times greater ($1.25^3$) than the dose received for the first zone (101), and the UV dose corresponding to this fourth zone is the MEDu amount.

FIG. 1B, still according to the prior art and with reference to this example, the fifth spot (115) of the protected zone is evaluated as being the first in the increasing order of exposure to cause erythema to appear, and the UV dose received by this fifth zone (115) of the protected portion is the MEDp amount.

Compared with the fourth zone (104) of the unprotected portion and according to this example, this fifth zone (115) received a UV dose 15 times greater than that at which the latter has been exposed (1.25×12). Thus, according to this example MEDp/MEDu=SPFi=15.

The same operation is performed on at least 10 subjects, in accordance with the standard, and the SPF value of the product is the arithmetic mean of the SPFi thus determined.

The system of the invention implements a multispectral analysis of the exposed zones and compares according to the modalities of the various implementations, the results from this multispectral analysis, for the protected zone and the unprotected zone.

Figure 7:
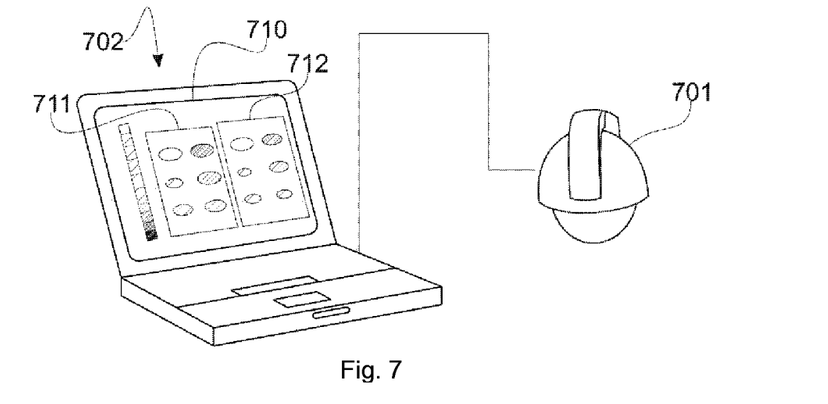
FIG. 7 schematically represents one example of embodiment of the system subject matter of the invention.

FIG. 7, the system of the invention comprises a multispectral camera (701), or any other equivalent acquisition device, capable of acquiring, in one single or in a plurality of shots of the zone of interest, an image in reflectance according to a plurality of separated wavelengths.

Thus, unlike a conventional digital photographic image that records the luminance of a scene according to three primaries (RGB) the pixels of the image obtained by the multispectral camera possess N primaries corresponding to N acquisition wavelengths of the multispectral camera used.

The multispectral imaging makes possible a more precise definition of the reflected light by adding nuances of color and information invisible to the naked eye.

Under the generic term of "multispectral camera" a plurality of acquisition technologies are possible, implementing or not specific lighting of the scene.

Advantageously, the scene analyzed, namely the skin of the subject on which the UV exposure has been performed, is lit up by a light source adapted during the acquisition of the image by the multispectral camera, this in order to ensure calibrated lighting conditions and an irradiance by all the wavelengths acquired by the camera. By way of example the light source comprises an integration sphere with a plurality of light-emitting diodes (LEDs), emitting in different wavelengths, corresponding to the acquisition wavelengths of the camera used. Thus, the lighting conditions are calibrated and always reproducible.

According to a non-limiting embodiment, the camera performs an acquisition according to 19 discrete wavelengths, ranging from 365 nanometers to 970 nanometers. The shortest wavelength corresponds to the ultraviolet region and the longest wavelengths (beyond 780 nm) to the infrared region. The intermediate wavelengths correspond to the visible light spectrum, from violet to infrared, and the lighting source comprises a plurality of LEDs the emission spectrum of which is within the acquisition spectrum.

As a minimum, the acquisition spectrum of the camera and the irradiance spectrum must make the acquisition possible according to a plurality of primaries distributed between 400 nm and 700 nm, zone wherein the reflectance/absorbance peaks of hemoglobin are located, and which appear (at different intensities) both on healthy skin (without erythema) and on skin having erythema.

The inventors were thus able to determine that suitable and reproducible results as disclosed in the example at the end of this document were obtained with a multispectral acquisition comprising at least 8 wavelengths covering 400 nm to 700 nm.

Thus, each pixel of an image recorded by the multi spectral camera of the system subject matter of the invention is a mixture of more than 8 primaries preferably more than 16 primaries, and according to one example of embodiment, comprises up to 19 primaries.

The image of each spot, acquired directly on the skin of the subject, and corresponding to an exposure to a UV dose, results in a luminance or reflectance intensity, or alternatively an absorbance, with absorbance=100-reflectance, and the analysis of the image by spectral de-mixing, such as described below, makes it possible to determine the share of this intensity attributable to an erythemal situation and as a result, to characterize the erythema.

Figure 2:
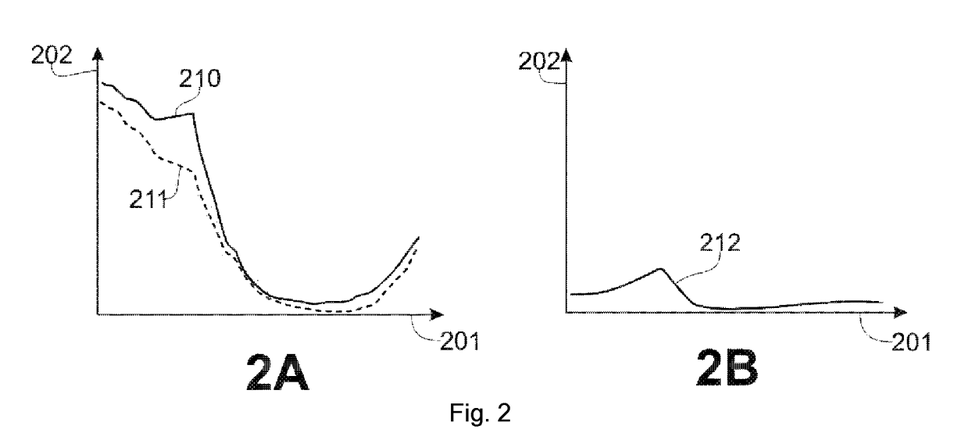

FIG. 2A compares the envelope of the spectrum (210) of a zone of skin having well-developed erythema, giving the absorbance (202) depending on the wavelength (201), with the envelope of the spectrum (211) of a so-called healthy zone of skin (without erythema).

The spectrum of the image of the erythemal zone is in reality the combination of the spectrum of healthy skin, and a modification of this spectrum by the presence of erythema.

FIG. 2B, by subtracting from the spectrum of the erythemal zone the spectrum of the healthy skin zone, the spectrum (212) of this modification attributable to the erythema is obtained. This particularly presents a more pronounced absorbance for the wavelengths close to 580 nm, characteristic of the absorbance of hemoglobin.

This spectrum (212) constitutes in a way the signature of erythema.

Thus, the image of an erythemal zone is analyzed by a spectral de-mixing process so as to extract therefrom the contribution of the erythema in terms of abundances in the spectral bands in accordance with this signature.

Spectral de-mixing techniques are known from the prior art and consist of breaking down the measured spectrum into a set of pure components (also called endmembers) and estimating the respective proportions (also called abundances) of each of these components. In other terms, the spectrum observed in each pixel is assumed to be equal to a combination of spectral signatures of a certain number of pure components, components of the healthy skin and components of the erythema, the aim being to evaluate the proportion of each of its components.

According to an exemplary embodiment, the method implemented by the system of the invention uses a linear spectral de-mixing technique, making the hypothesis that in each pixel the measured spectrum corresponds to the weighted average (depending on abundances) of the spectral signatures of the pure components (healthy skin and erythema).

Thus, without going into more detail, spectral de-mixing consists of expressing a measured spectrum y depending on pure components by an equation of type y=Ma+n, where M is the matrix of spectral signatures of the pure components, a is the vector of the abundances and n is a Gaussian disturbance, the unknown being the vector of the abundances a.

In the case of the invention, there are two pure components or endmembers: the healthy skin and the erythema. An example of spectrum corresponding to the healthy skin (211) is given FIG. 2A and an example of spectrum corresponding to the erythema (212) is given FIG. 2B.

The solution of the equation is obtained by a constrained regression algorithm aiming to minimize the residues r such as r=y−Ma.

According to an example of implementation, the method implemented by the system of the invention uses for this purpose a so-called parsimonious algorithmic method, such as the SUnSAL, acronym for "Sparse Unmixing by variable Splitting and Augmented Lagrangian" method.

The application of this method on a multispectral image of a zone of skin exposed or not to UV and having or not an erythema makes it possible, in a way, to classify the pixels of this image into a "healthy skin" class and an "erythema" class.

Figure 3:
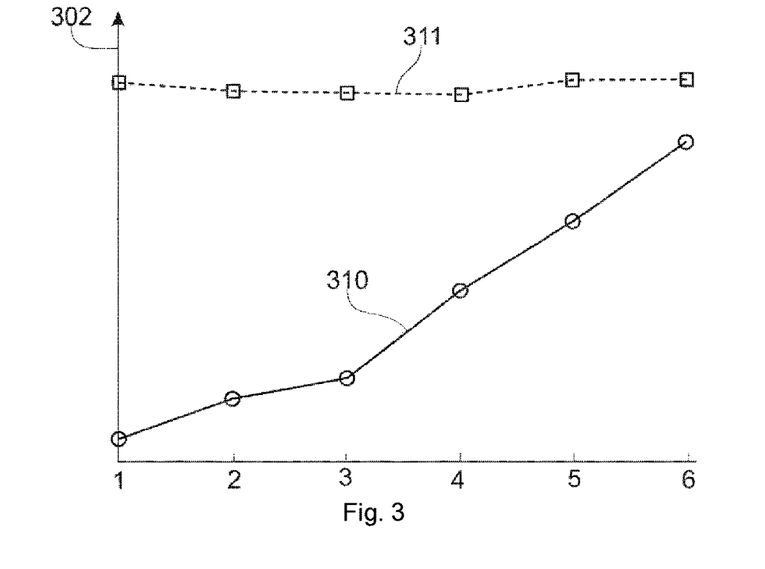
FIG. 3 gives an example of response curves depending on the UV dose received, by separating the healthy skin component and the erythemal component.

FIG. 3, the processing described above is applied on 6 zones having been exposed to UV according to increasing doses from zone 1 to zone 6, as shown in FIG. 1A or FIG. 1B.

The image processing makes it possible to determine for each of these zones the intensity of the absorbance (302) corresponding to the healthy skin (311) and to the erythema (310). This last curve (310) shows the increasing relative abundance of the spectral signature of the erythema when the UV dose to which the zone has been exposed increases.

This result shows the relevance of the spectral de-mixing applied, the intensity (311) corresponding to the healthy skin being substantially constant regardless of the intensity of the erythema.

The curve (310) corresponding to the intensity of the absorbance associated with an erythemal situation is increasing with the order number of the spot exposed, that is to say with the UV dose. In addition, this curve (310) is representative of the erythemal response of the skin depending on the received UV dose.

For the implementation of the system of the invention only the erythemal response curve (310) is necessary, the curve (311) corresponding to the healthy skin (without erythema) only being represented in FIG. 3 to show the relevance of the spectral de-mixing operation performed, or is only used according to improved embodiments.

Figure 4:
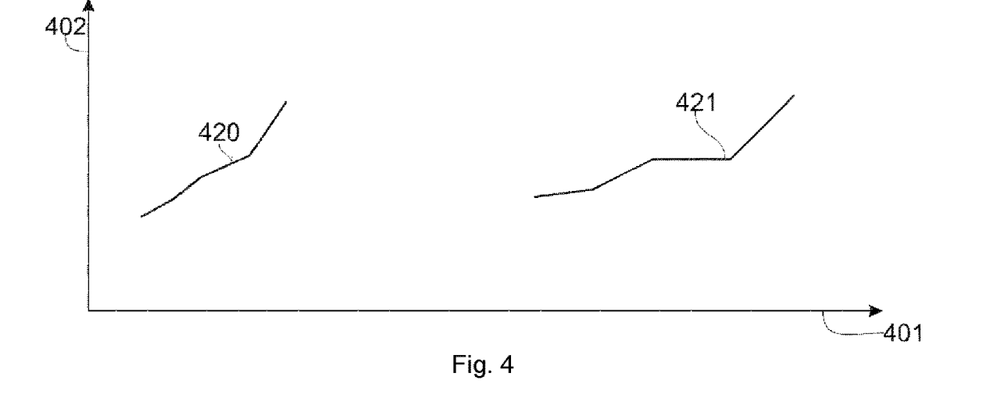
FIG. 4 shows an example of response curves of the erythemal components of a protected zone and of an unprotected zone depending on the UV dose of exposure.

FIG. 4, by applying the spectral de-mixing method on a multispectral image acquisition performed on the skin without protection, as in FIG. 1A, and on an acquisition performed on a protected zone as in FIG. 1B, two intensity curves of the absorbance (402) are obtained depending on the UV dose (401), the curve (420) corresponding to an erythemal response curve for the unprotected zone, corresponding naturally to UV doses lower than those of the erythemal response curve (421) of the protected zone, the erythema appearing in the protected zone for higher UV doses.

The deviation between these response curves (420, 421) is representative of the SPFi of the product tested.

The two response curves (420, 421) corresponding respectively to the zone without protection and to the protected zone, do not necessarily have exactly the same shape, but have a certain degree of homothety.

The curve $\varphi_p$ (420) is the response curve of the unprotected zone, and the curve $\varphi_p$ (421) is the response curve of the protected zone.

These curves respectively represent the intensity of the absorbance of the erythemal component of the skin depending on the UV dose at which it has been exposed. Thus, the curve ($\varphi_n(u_n)$) gives the intensity of the erythema depending on the UV dose, $u_n(i)$, received by each spot i=1 . . . 6 of the unprotected zone, and $\varphi_p(u_p)$ gives the intensity of the erythema according to the UV dose, $u_p(i)$, received by each spot i=1 . . . 6 of the zone protected by the photoprotective product.

By assuming that the photoprotective product has an expected minimum protection index $SPF_0$, $u_p(i)=u_n(i)\cdot SPF_0$.

In order to determine the SPFi, it is considered that the photoprotective product absorbs, reflects or scatters a portion of the UV radiation and only allows a proportion 1/k of this radiation to reach the skin.

The response of the skin is only controlled by the UV dose effectively received. This hypothesis is fully compliant with the ISO 24444:2010 standard. Thus, a zone of skin protected by the photoprotective product tested and exposed to a dose u receives an effective radiation dose u/k.

For the implementation of the system of the invention in compliance with the ISO standard, the UV doses to which the protected portion and the unprotected portion are exposed must have been selected beforehand so as to cause at least one erythema corresponding to the definition of the ISO 24444:2010 standard to appear in each of these zones, that is to say perceptible unambiguous erythema having regular borders and appearing on most of the site (spot) of UV exposure, within the 16 hours to 24 hours following this exposure.

The system of the invention determines the factor k, interpretable as a homothety factor between the two curves, by comparing the response curves (420, 421) according to one or more methods such as disclosed below, taken alone or in combination.

Figure 5:
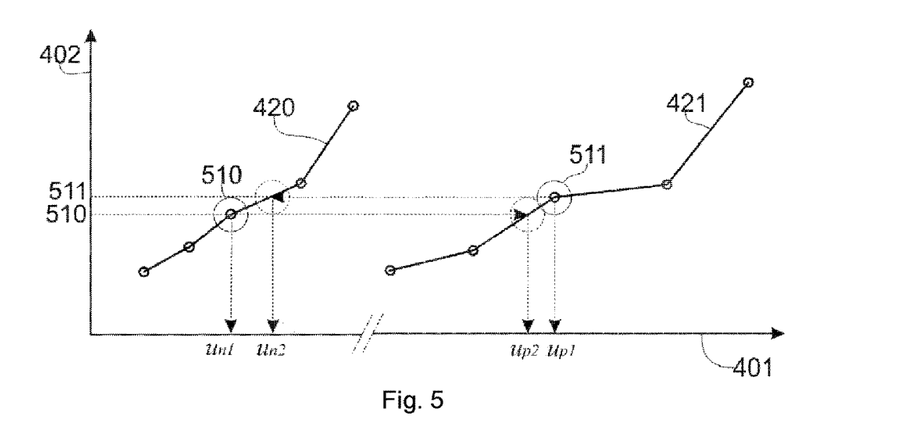
FIG. 5 illustrates an example of determining the SPFi of a photoprotective product from the response curves of FIG. 4, implementing a detection of the MED for the protected zone and for the unprotected zone.

FIG. 5 illustrates a plurality of methods that can be used for this purpose.

According to a first example of implementation, the method implemented by the system of the invention remains fully compliant with the ISO 24444:2010 standard and involves visually determining the MEDu and the MEDp Thus, the intensity (510) of the erythemal components of the spot corresponding to the MEDu is determined on the zone without protection, in the same way as the intensity (511) corresponding to the MEDp for the protected zone. To each of these intensities corresponds a UV dose, $u_{n1}$, $u_{p1}$.

By reporting on the response curve of the unprotected zone (420) the intensity (511) corresponding to the MEDp identified on the protected zone, and by reporting on the response curve of the protected portion (421) the intensity (510) corresponding to the MEDu, it is possible to define the values $u_{n2}$ and $u_{p2}$, corresponding respectively to the UV dose, leading on the unprotected zones to erythema of intensity equivalent to that corresponding to the spot of the protected zone for which the MEDp is detected and vice versa.

In this example of implementation SPFi is given, for example, by the ratio $SPFi=(u_{p1}+u_{p2})/(u_{n1}+u_{n2})$.

Compared with the method of the prior art, this method that is carried out in a way similar to double weighing, improves the precision and the reproducibility of the SPFi determination.

Figure 6:
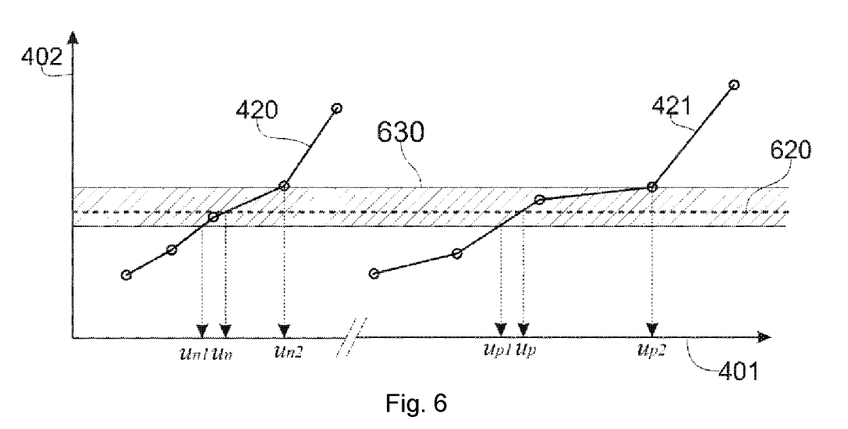
FIG. 6 illustrates an example of determining the SPFi of a photoprotective product from the response curves of FIG. 4, implementing a threshold or a band of erythemal intensity.

FIG. 6, according to another example of implementation, a threshold (620) or a band (630) of intensity corresponding to the presence of significant erythema are determined from statistical data or by learning. The intersections of the threshold (620) or of this band (630) with each of the response curves make it possible, to determine a k value and thus to obtain SPFi.

According to one embodiment the learning algorithm is optimized and parameterized beforehand from a reference image bank annotated with the clinical scores of the MED Thus, by referring to FIG. 6, $SPFI=(u_p/u_n)$ in the case of an estimation by a threshold (620) or $SPFi=(u_{p1}+u_{p2})/(u_{n1}+u_{n2})$ in the case of an estimation by a band (630).

FIG. 6 represents a threshold (620) and a band (630) the features of which are constant depending on the UV dose (401).

According to a preferred embodiment, the method implemented by the system subject matter of the invention determines the k value from the set of response curves, $\varphi_p(u_n)$ of the unprotected portion (420) and $\varphi_p(u_p)=\varphi_p(k\cdot u_n)$ of the protected portion (421), that being the k value that minimizes the square deviation between the 2 curves which amounts to minimizing the amount:

$$\int_{min(u)}^{max(u)} (\varphi_n(u)-\varphi_p(k\cdot u))^2 \cdot du$$

where u is the UV dose.

In order to perform this operation, the response curves $\varphi_n$, $\varphi_p$ are approximated by sigmoids $f_n$, $f_p$ and the mathematical formulation becomes:

$$\int_{min(u)}^{max(u)} (f_n(u)-f_p(k\cdot u))^2 \cdot du$$

where the k value minimizing this amount is equal to SPFi.

Thus, according to this embodiment, the method implemented by the system subject matter of the invention does not require the determination of MEDu and of MEDp, or any learning, thus dispensing with uncertainties on this determination and performs the evaluation of the SPFi on the set of exposed spots, both for the unprotected portion and the protected portion.

FIG. 7, regardless of the embodiment, the system of the invention comprises a multispectral camera (701) and processing means (702) for example in the form of a microcomputer.

The microcomputer conventionally comprises memory means, input and pointing means such as a keyboard and a mouse, display means such as one or more screens and a microprocessor.

The microcomputer (702) is connected to the multispectral camera (701). According to alternative embodiments, this connection is a wired link, the images acquired by the camera being transmitted directly to the microcomputer, which according to one example of embodiment also controls the acquisition performed by the camera, a wireless connection such as WIFI® or Bluetooth® the microcomputer and the multispectral camera being members of the same personal network or WPAN, or also via a network connection of WAN type or a connection via the Internet. This last embodiment makes it possible to perform the acquisition and the processing of information in remote sites and/or temporally shifted so as to, for example, perform acquisitions and processing in batches.

Advantageously, the images transmitted by the multispectral camera comprise a metadata file comprising all or part of the information concerning the conditions for acquiring the image, the product tested, in coded form, the subject in coded form, particularly their individual typological angle characterizing the color of their skin, the UV doses corresponding to the various exposed zones, the dimension of the exposed zones. The data relating to the subject and to the product are for example entered during the acquisition of the images for example by scanning a smart code, such as a barcode or a QR code.

In particular, this information makes it possible, via the analysis of these data to associate within the microcomputer an acquisition relating to the unprotected skin and an acquisition relating to the protected skin, then to group the processing results in the aim of calculating the SPF.

The information relating to the subject and to the product are coded, so that the analysis of the results is performed "blind" in accordance with the standard.

The microcomputer comprises in its memory means or via a network access to a shared application, a program for processing images from the multispectral camera in order to perform the spectral de-mixing of an image, preferably via the SUnSAL method, and to isolate the component attributable to erythema in said images.

A classification program makes it possible from the results of the image processing program to determine the response curve (420, 421 FIGS. 4 to 6) corresponding to each of these acquisitions.

Following the performance of this processing, the aforementioned microprogram or an additional display program makes it possible to display an image (710) in false colors showing the intensity of the erythemal component on the various spots of the zones acquired and to compare the results obtained on the protected zone (711) and on the unprotected zone (712).

The display of this image makes it possible, furthermore, to facilitate the determination of the MEDu and of the MEDp by visually reinforcing the erythemal component. The image processing makes it possible not only to return intensity information of the erythema, via the display of false colors, but also spatial information on the extent of the erythemal zone within each spot, which facilitates the determination of the zones corresponding to the MEDu and to the MEDp.

Thus, according to a first embodiment, the analyst points the zone (spot) corresponding according to them to the MEDu, then the zone (spot) corresponding to the MEDp.

Still according to this first embodiment, after validation, the program extracts data files corresponding to the UV doses associated with these zones and calculates the SPFi by using the response curves as presented above with reference to FIG. 5, before storing the value thus obtained in a result file.

According to another embodiment, the SPFi is determined from a threshold or from a band such as illustrated with reference to FIG. 6. For this purpose the threshold or the band, or more advantageously a plurality of thresholds or a plurality of bands are stored in the memory means of the computer device (701) associated for example with the skin color features. The selection of the threshold or of the suitable band is performed based on metadata transmitted with the images.

According to another embodiment, the response curves of the protected portion and of the unprotected portion are approximated by sigmoids and the SPFi of the product is determined by a program aiming to minimize the mean square deviation between the response curve of the protected zone and the response curve of the unprotected zone assigned with a k coefficient, k being the SPFi. This embodiment makes it possible to automate the determination of the SPFi by the analysis of images.

Part or all of these embodiments are advantageously combined and thus provide for a given acquisition, a plurality of values of the SPFi. According to this combined example of embodiment, the value of the SPFi obtained is considered valid if the plurality of values corresponding to the various methods is included within an interval, for example +/−10% centered on the average value of the plurality.

After processing all of the valid results corresponding to the product tested and stored in the result file, they are used to determine the SPF of the product.

The method implemented by the system of the invention is improved if in addition to the zones exposed to the irritation, regardless of the cause of this irritation (UV exposure or to a product during topical application), the acquisition of a healthy zone of skin, close to the test zone, is performed. Thus, this acquisition is advantageously used to determine the spectral components of the erythema, as disclosed with reference to FIG. 2, or to control the validity of the response curves as disclosed with reference to FIG. 3.

Advantageously, the acquisition performed on healthy skin is associated with a test pattern. This embodiment makes it possible, among other things, to determine by processing images the color of the skin of the subject.

The examples of embodiment disclosed above are mainly disclosed within the scope of determining the sun protection factor of a photoprotective product, however all or part of the principles and of the embodiments disclosed can be used for characterizing erythemal zones within the scope of other skin irritation tests, implementing comparisons of erythemal zones or comparisons between irritated zones and healthy zones.

The possibility of automatically characterizing zones subjected to the irritation test by means of the device and of the method the invention makes it possible for certain applications to rapidly and reliably process a large number of tests.

Thus, the method and the system of the invention are advantageously used for systematic tests within the scope of screening ingredients likely to enter in the composition of a topical application product, in relation to the irritating power of these ingredients or of their protective effect.

EXAMPLE

In order to test the validity of the method, a study for determining the SPFi of a product, referenced P2 in the ISO 24444:2010 standard, is performed on 10 subjects.

Each subject is thus exposed to UV on 2 zones in the back, first zone without photoprotective agent, a second with the photoprotective product P2. This product consists of 3 phases, phase 1: lanolin 4.5%; *Theobroma cacao* seed butter 2.0%; glycerol monostearate 3.0%; stearic acid 2.0%; 2-ethylhexyl 4-(dimethylamino) benzoate PABA (CAS 21245-02-3) 7.0%; benzophenone-3 (CAS 131-57-7) 3.0%; phase 2: water 71.6%; sorbitol (70% of liquid) 5.0%; triethanolamine 1.0%; methylparaben 0.3%; propylparaben 0.1%; phase 3: benzyl alcohol 0.5%. The data corresponding to the mass fractions (%). Each exposure zone consists of 6 spots with a progression of doses of 1.25 (in accordance with the standard). For each subject zone 2 (with photoprotective product) has been exposed to doses 14 times greater than zone 1. The exposure system used is UV SOLAR LIGHT MULTIPORT BERGER (model 601 of 300 W) the spectrum of which is compliant with the standard.

Twenty-four hours after the exposure, each zone of each subject is subjected to a multispectral acquisition by means of the device subject matter of the invention comprising a multispectral camera with 19 wavelengths between 365 nm and 970 nm, and the value of the SPFi corresponding to each of the subjects is determined by comparing the response curves of the protected portion and of the unprotected portion after spectral de-mixing and extraction of the erythemal component.

The distribution of the acquisition wavelengths of the camera is given in Table 1 below.

| Band no. | Name of the band | Wavelength [nm] |
|---|---|---|
| 1 | UVA | 365 |
| 2 | Violet | 405 |
| 3 | Indigo | 435 |
| 4 | Blue | 450 |
| 5 | Blue | 470 |
| 6 | Cyan | 505 |
| 7 | Green | 525 |
| 8 | Yellow | 570 |
| 9 | Amber | 590 |
| 10 | Red | 630 |
| 11 | Red | 645 |
| 12 | Red | 660 |
| 13 | Dark Red | 700 |
| 14 | Near Infrared | 780 |
| 15 | Near Infrared | 850 |
| 16 | Near Infrared | 870 |
| 17 | Near Infrared | 890 |
| 18 | Near Infrared | 950 |
| 19 | Near Infrared | 970 |

The corresponding results of the calculation of the FPSi are given for each subject in Table 2 below.

| Subject No. | FPSi |
|---|---|
| 1 | 11.8 |
| 2 | 17.4 |
| 3 | 7.2 |
| 4 | 18.2 |
| 5 | 23.4 |
| 6 | 16.4 |
| 7 | 15.4 |
| 8 | 17.6 |
| 9 | 15.4 |
| 10 | 17.8 |

The arithmetic mean of the SPFi provides the value of the SPF of the product, namely an SPF of 16.06.

This value of 16.06 corresponds to the reference value of the standard for the product P2 that is 16.1, which standard indicates in its Annex C an average SPF of 16.1 and between 13.7 and 18.5.

This example shows the relevance of the method subject matter of the invention for automatic determining a SPFi.

The invention claimed is:

1. A method for determining an individual solar protection factor (SPFi) of a photoprotective product from two series of images, each series comprising a same number of spots obtained by exposing a skin of an individual to increasing UV doses, a first series obtained from a skin without protection and a second series obtained from the skin protected by the photoprotective product, the two series causing an erythema on at least one of its spots, comprising:
   acquiring a multispectral image of each series, each pixel of the multispectral image comprising at least 8 primaries with a wavelength comprised between 400 nm and 700 nm;
   on each multispectral image, performing a spectral de-mixing to obtain for each spot of said each series an intensity of spectral components corresponding to an erythema;
   obtaining for each series a response curve providing an intensity of the spectral components corresponding to an erythema depending on the increasing UV doses of each series;
   approximating the response curve of each series by a sigmoid function in the form of a function $f_n$, for the response curve of the series corresponding to the non-protected skin and a function $f_p$ for the curve corresponding to the series corresponding to the skin protected by the photoprotective product;
   determining a k value minimizing a mean square deviation between functions $f_n$, $f_p$ over a range from a lowest UV dose to a highest UV dose of exposure of each series; and
   assigning the k value to the SPFi.

2. The method of claim 1, comprising the acquisition of a multispectral image of a zone of healthy skin without erythema of the individual and determining the spectral components corresponding to an erythema by subtracting a spectrum of the healthy skin of the individual to a spectrum of a skin of the individual with an erythema.

3. The method of claim 1, further comprising adding metadata relating to conditions for forming erythemal zones and to conditions for acquiring the multispectral images to a multispectral image file.

4. A method for determining a Solar Protection Factor (SPF) of a photoprotective product, comprising the steps of:
   repeating the method of claim 1 for a plurality of at least 10 individuals;
   recording a value of SPFi for each individual; and
   determining a value of the SPF of the photoprotective product as an average of the recorded SPFi values.

* * * * *